United States Patent
Quinn

(10) Patent No.: US 6,393,094 B1
(45) Date of Patent: May 21, 2002

(54) METHODS AND APPARATUS USING ATTENUATION OF RADIATION TO DETERMINE CONCENTRATION OF MATERIAL IN OBJECT

(75) Inventor: Alan P. Quinn, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/830,456

(22) PCT Filed: Sep. 29, 1999

(86) PCT No.: PCT/US99/22680

§ 371 Date: Apr. 26, 2001

§ 102(e) Date: Apr. 26, 2001

(87) PCT Pub. No.: WO00/28310

PCT Pub. Date: May 18, 2000

Related U.S. Application Data

(60) Provisional application No. 60/107,431, filed on Nov. 6, 1998.

(51) Int. Cl.$^7$ ............................................... G01B 15/02
(52) U.S. Cl. ....................................................... 378/54
(58) Field of Search ...................................... 378/53–56

(56) References Cited

U.S. PATENT DOCUMENTS 4,618,975 A    10/1986   Glatschnig ................... 378/51
6,148,059 A  * 11/2000   Quinn ........................ 378/45

FOREIGN PATENT DOCUMENTS

EP           0 249 738 A1    5/1987   .......... G01N/22/04

OTHER PUBLICATIONS

Patent Abstracts of Japan, Publication No. 60250225 dated Dec. 10, 1985, Furukawa Electric Co. Ltd (Application No. 59106803).

* cited by examiner

*Primary Examiner*—Craig E. Church
(74) *Attorney, Agent, or Firm*—Robert L. Carlson

(57) ABSTRACT

An apparatus for determining dopant concentration in soot that constitutes at least a portion of a soot preform used to form an optical waveguide includes a weight-measuring device, a thickness-parameter-measuring device, a radiation source, a radiation sensor, and a determination device. The weight-measuring device measures the weight of the soot preform. The thickness-parameter-measuring-device measures a thickness parameter of the soot preform. The radiation source irradiates the soot with penetrating radiation. The radiation sensor detects intensity of penetrating radiation passing through the soot. The determination device determines a concentration of dopant in the soot based on the detected intensity of penetrating radiation and the measured weight and thickness parameter.

12 Claims, 4 Drawing Sheets

METHODS AND APPARATUS USING ATTENUATION OF RADIATION TO DETERMINE CONCENTRATION OF MATERIAL IN OBJECT

This Application is a 371 of PCT/U.S. Ser. No. 99/22680 filed Sep. 29, 1999, which claims benefit of Prov. No. 60/107,431 filed Nov. 6, 1998.

BACKGROUND OF THE INVENTION

1. Field of the Invention

The present invention relates to methods and apparatus using attenuation of penetrating radiation to determine a concentration of material in an object. More specifically, the present invention relates to methods and apparatus using X-ray attenuation to determine a concentration of dopant in a soot preform used to form optical waveguide fibers ("optical fibers").

2. Description of the Related Art

An optical fiber typically includes a cladding made of pure silica ($SiO_2$) and a core made of silica doped with germania ($GeO_2$). The germania dopant alters the refractive index of the silica in the core. Portions of the core often contain different concentrations of germania, resulting in different refractive indexes along the diameter of the core. The distribution of refractive indexes along the diameter of the core (i.e., the refractive-index profile) determines operating characteristics of the optical fiber.

The optical fiber can be formed by a conventional process known as outside vapor deposition ("OVD"). Generally, the OVD process involves forming a soot preform by burning a gaseous mixture to produce soot containing silica and germania, successively depositing layers of that soot onto a mandrel rod to form a core portion of the soot preform, burning a gaseous mixture to produce soot containing only silica, and successively depositing layers of that soot onto the core portion to form a cladding portion of the soot preform. The soot preform is consolidated by sintering to form a glass blank. An optical fiber is drawn from the glass blank. The concentrations of germania in the soot layers forming the core portion primarily determine the concentrations of germania along the diameter of the core of the resulting optical fiber.

Japanese Patent Application No. 59-106803 (Hara) and U.S. Pat. No. 4,618,975 (Glantschnig) disclose techniques that use X-ray attenuation to nondestructively evaluate the concentrations of germania in soot preforms. Both approaches measure X-ray attenuation at two energies. Hara's scheme relies upon the fact that the dopant (Ge) to matrix (Si) attenuation ratio changes with X-ray photon energy. Hara's scheme is not particularly sensitive for soot preforms, however, because the ratio is nearly constant over any practical X-ray energy range. Glantschnig's method is based on the fact that the ratio of dopant attenuation (absorption) to density attenuation (scattering) changes with X-ray photon energy. Like Hara's ratio, Glantschnig's ratio is nearly constant over an energy range practical for soot preforms. Thus, Glantschnig's method confounds density changes with dopant concentration changes.

SUMMARY OF THE INVENTION

As embodied and broadly described herein, the invention comprises a method of determining a concentration of dopant in soot that constitutes at least a portion of a soot preform used to form an optical waveguide. The method includes the steps of measuring the weight of the soot preform, measuring a thickness parameter of the soot preform, irradiating the soot with penetrating radiation, detecting intensity of penetrating radiation passing through the irradiated soot, and determining the concentration of dopant based on the measured weight, the measured thickness parameter, and the detected intensity of penetrating radiation.

Another aspect of the present invention comprises a method of determining a concentration of dopant in first and second segments of soot that constitute at least a portion of a soot preform used to form an optical waveguide. The method includes the steps of measuring the weight of the soot preform after the first segment of soot has been deposited on the soot preform, measuring a thickness parameter of the soot preform after the first segment of soot has been deposited on the soot preform, measuring the weight of the soot preform after the second segment of soot has been deposited on the soot preform, measuring a thickness parameter of the soot preform after the second segment of soot has been deposited on the soot preform, irradiating the second segment of soot with penetrating radiation, detecting intensity of penetrating radiation passing through the second segment of soot, determining the concentration of dopant in the second segment of soot based on the detected intensity of penetrating radiation passing through the second segment of soot and the measured weight and thickness parameter of the soot preform after the second segment of has been deposited on the soot preform, irradiating the first and second segments of soot with penetrating radiation, detecting intensity of penetrating radiation passing through the first and second segments of soot, and determining the concentration of dopant in the first segment of soot based on the detected intensity of penetrating radiation passing through the first and second segments of soot and the measured weight and thickness parameter of the soot preform after the first segment of soot has been deposited on the soot preform.

Yet another aspect of the present invention includes an apparatus for determining dopant concentration in soot that constitutes at least a portion of a soot preform used to form an optical waveguide. The apparatus comprises a weight-measuring device that measures the weight of the soot preform, a thickness-parameter-measuring device that measures a thickness parameter of the soot preform, a radiation source that irradiates the soot with penetrating radiation, a radiation sensor that detects intensity of penetrating radiation passing through the soot, and a determination device that determines a concentration of dopant in the soot based on the measured weight and thickness parameter, and the detected intensity of penetrating radiation.

A particularly preferred embodiment of the invention quantifies the soot density profile by successively measuring preform weight and preform diameter during soot deposition, measuring X-ray attenuation of the preform (during or after soot deposition), and computing dopant concentration profile from the solution of an attenuation equation.

It is to be understood that the foregoing general description and the following detailed description are exemplary and explanatory only and are not restrictive of the invention as claimed.

BRIEF DESCRIPTION OF THE DRAWINGS

The accompanying drawings illustrate one embodiment of the invention and together with the description serve to explain the principles of the invention.

DETAILED DESCRIPTION OF THE PREFERRED EMBODIMENT

Figure 1:
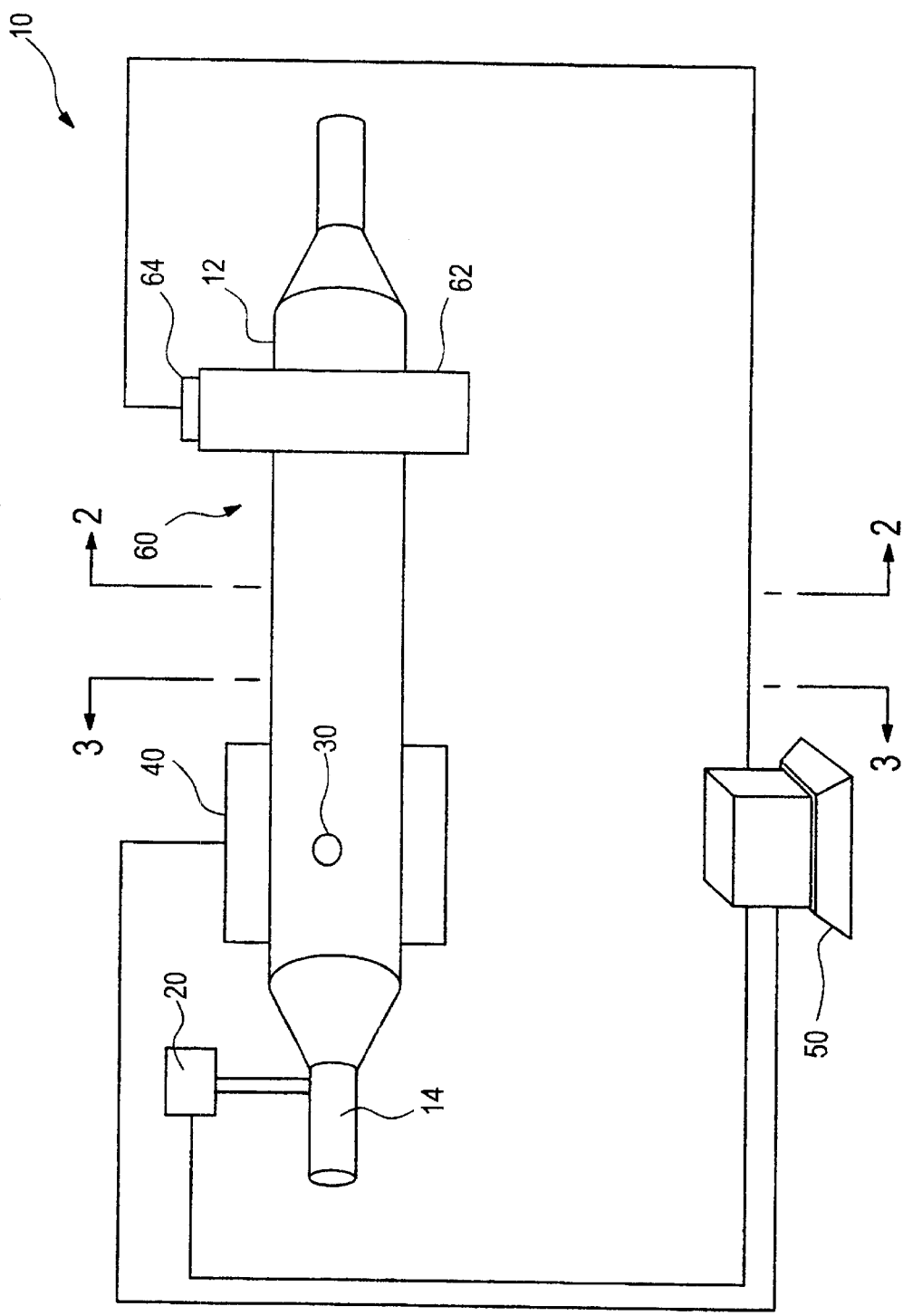
FIG. 1 is a side view of an embodiment of an apparatus according to the present invention for determining a concentration of dopant in a soot preform.

Reference will now be made in detail to the presently preferred embodiment of the invention. Wherever possible, the same reference numbers will be used throughout the drawings to refer to the same or like parts.

In general, the present invention determines the concentration of a dopant in a soot preform by measuring the weight of the soot preform, measuring a thickness parameter of the soot preform, irradiating the soot preform with penetrating radiation, and measuring the intensity of penetrating radiation passing through the soot preform. Using the measured weight, thickness parameter, and intensity, the present invention determines the dopant concentration in a segment of soot in the soot preform.

FIGS. 1 to 4 illustrate a preferred embodiment of an apparatus 10 according to the present invention for determining a concentration of dopant in a soot preform 12. The apparatus 10 includes a weight-measuring device 20, a thickness-parameter-measuring device 60, a radiation source 30, a radiation sensor 40, and a determination device 50.

The weight-measuring device 20 measures the weight of the soot preform 12 and provides a corresponding signal to the determination device 50. A preferred weight-measuring device 20 includes a resistance load cell connected to one end of a mandrel rod 14 upon which the soot preform 12 is formed. The other end of the mandrel rod 14 can be chucked to a drive motor (not shown).

Preform weight is recorded continuously during soot laydown. Variations due to preform runout are eliminated by averaging the individual load cell readings acquired during a preform rotation or an integral number of preform rotations. Variations due to preform traverse location are accommodated by synchronizing weight acquisition with preform traverse location. In other words, although the weight measurements are preferably continuous, an identifier or flag is associated with the starting point of pertinent weight measurements for each traverse, and the starting point is the same in each traverse. Preform weight at a given segment is the average of these synchronized, averaged readings. Weight of a segment is the weight gain observed since the previous segment.

Preferably, the weight-measuring device 20 measures the weight of the soot preform 12 numerous times during the formation of the soot preform 12. For example, the weight-measuring device 20 can measure the weight of the soot preform 12 each time a predetermined number of soot layers has been deposited during the formation of the soot preform 12.

Figure 2:
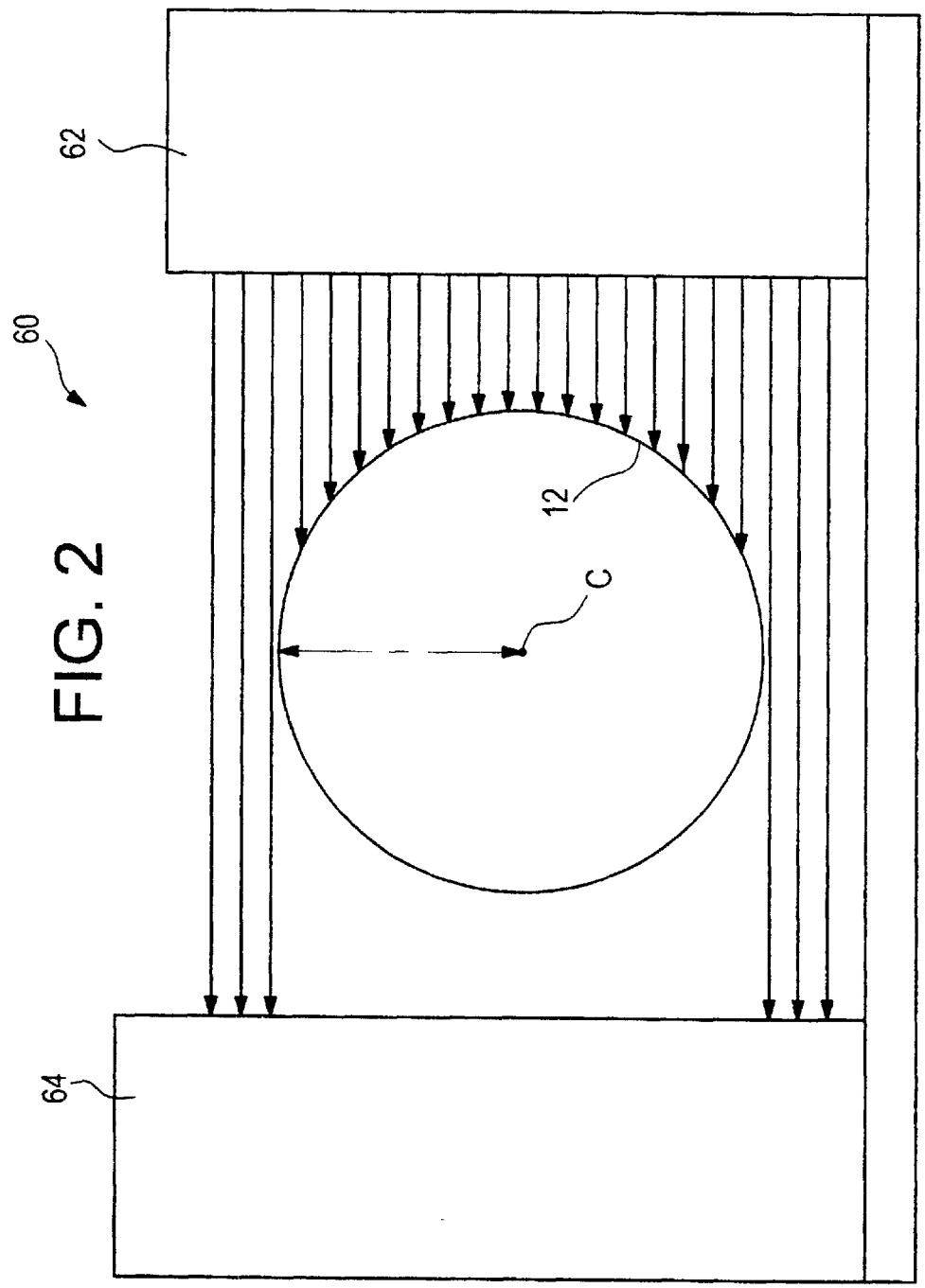
FIG. 2 is a cross-sectional view taken along line 2—2 of FIG. 1 showing a thickness-parameter-measuring device.

The thickness-parameter-measuring device 60 measures a thickness parameter, such as the radius or diameter, of the soot preform 12. Although the thickness-parameter-measuring device 60 is shown offset to the right in FIG. 1 for ease of illustration, it preferably measures a center portion of the soot preform 12. As shown in FIG. 2, the thickness-parameter-measuring device 60 can be a laser shadowing micrometer that includes a source 62 that emits optical beams and a detector 64 that detects optical beams emitted by the source 62. Based on the detected optical beams, the detector 64 provides a signal to the determination device 50. This information permits a thickness parameter, preferably the radius T, of the soot preform 12 to be determined by conventional mathematics. Commercially available devices that can perform this function include Anritsu KL-154A and Keyence LS-5001.

Preferably, the thickness-parameter-measuring device 60 measures the thickness parameter of the soot preform 12 numerous times during the formation of the soot preform 12. For example, the thickness-parameter-measuring device 60 can measure the thickness parameter of the soot preform 12 each time a predetermined number of soot layers has been deposited during the formation of the soot preform 12. Even more preferably, the thickness parameter is measured each time the weight of the soot preform is measured by the weight-measuring device 20.

The radiation source 30 irradiates the soot preform 12 with penetrating radiation. As used herein, the term penetrating radiation is intended to refer to radiation with the ability to penetrate and pass through relatively short lengths of soot. Five to one hundred KeV X rays are a preferred type of penetrating radiation. The source of X rays could be a point X-ray tube source that produces a fan beam that illuminates the full cross section of the soot preform 12. Preferably a micro focus, 100 KeV X-ray tube of 10 to 50 micron spot size, such as those produced by Philips, Kevex, or Pantak is used as the radiation source 30.

Figure 3:
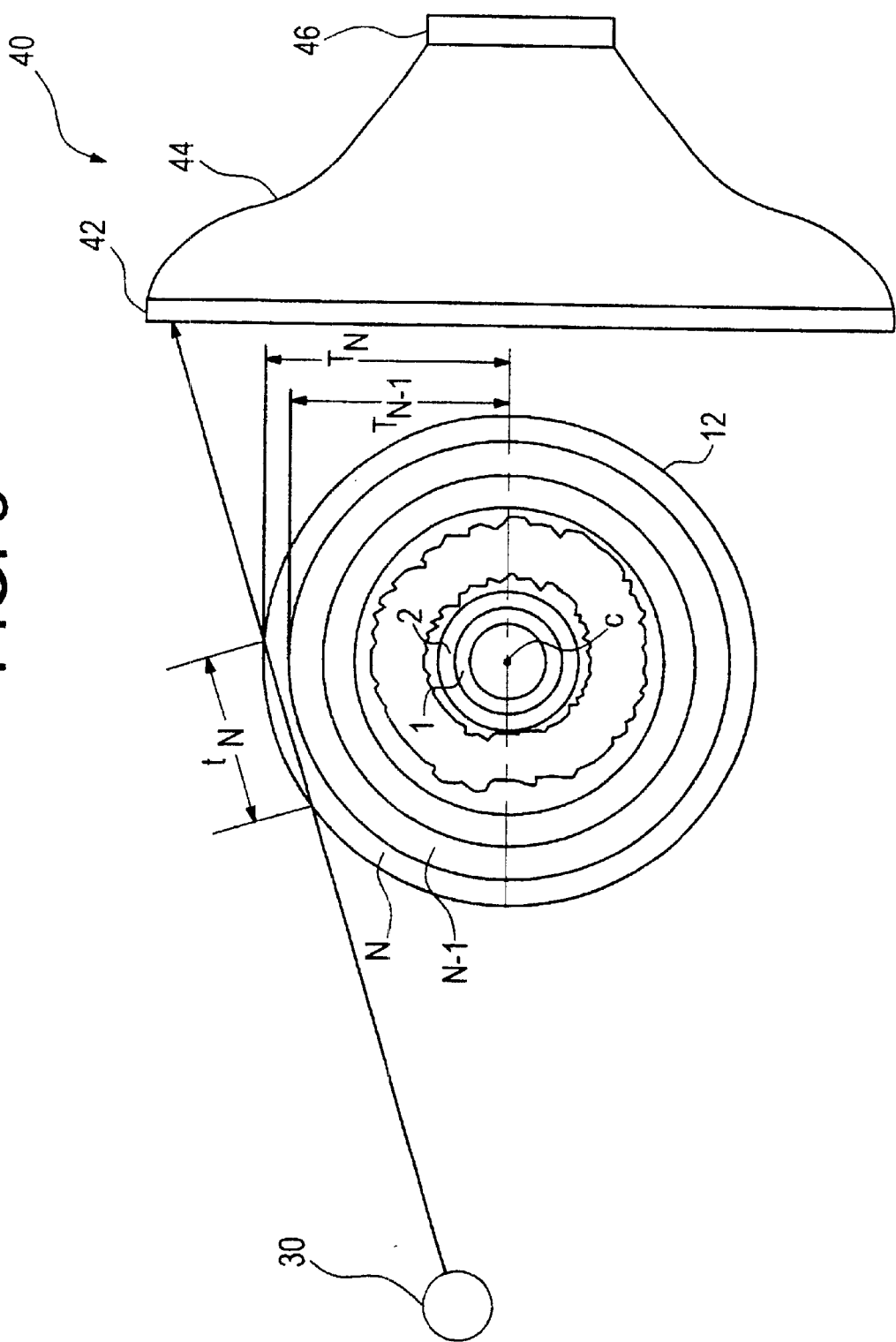
FIG. 3 is a cross-sectional view taken along line 3—3 of FIG. 1 showing a radiation source irradiating a segment N of the soot preform with penetrating radiation that is detected by a radiation sensor.
Figure 4:
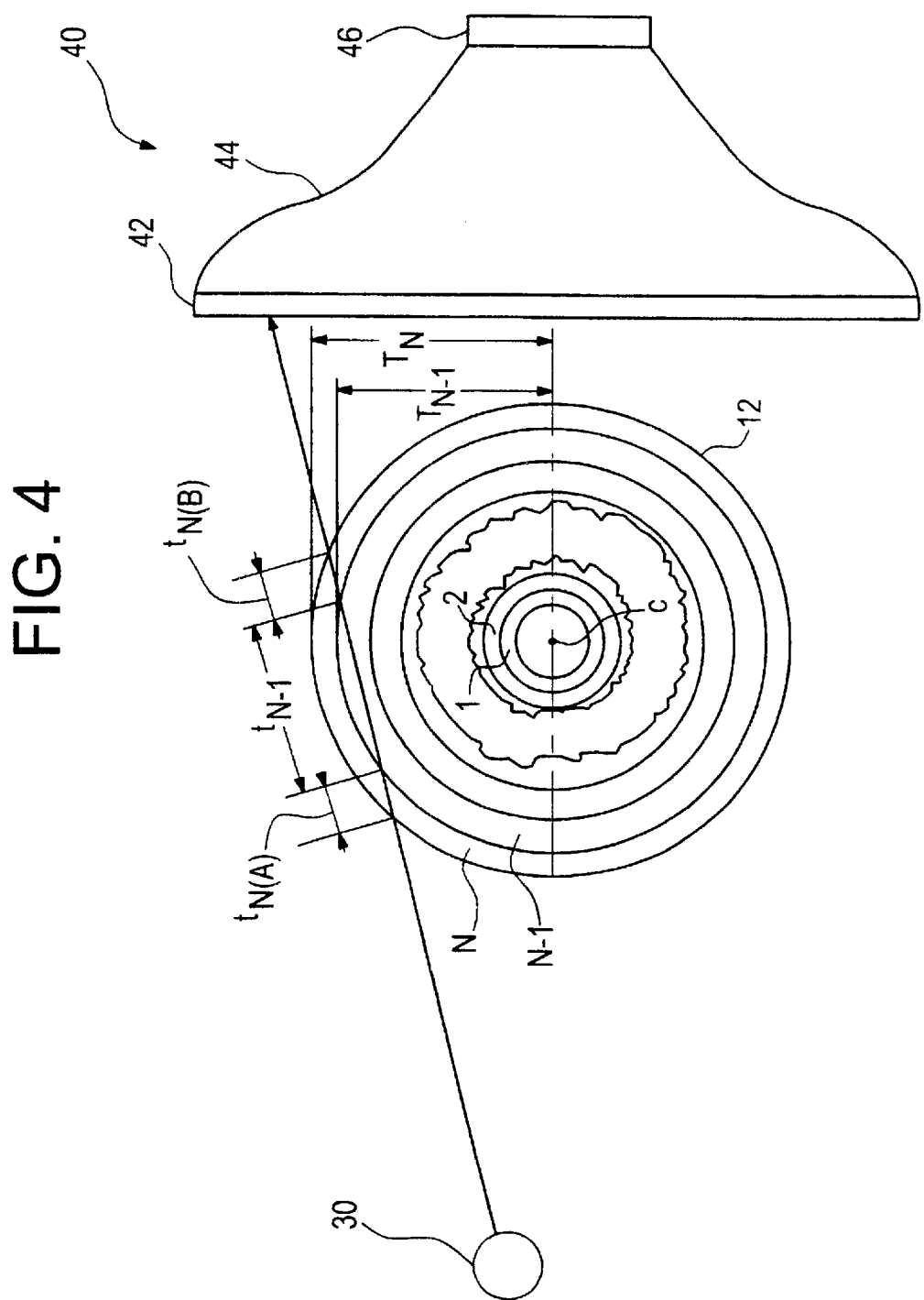
FIG. 4 is a cross-sectional view taken along line 3—3 of FIG. 1 showing the radiation source irradiating segments N and N−1 of the soot preform with penetrating radiation that is detected by the radiation sensor.

The radiation sensor 40 detects the intensity of penetrating radiation passing through the soot preform 12 and provides a corresponding signal to the determination device 50. A preferred radiation sensor 40 includes a pixelated detector, such as, a 4"×4" phosphor screen 42 and a tapered fiber optic bundle 44 that guides light pulses from the screen 42 to a CCD camera 46, as shown in FIGS. 3 and 4.

For ease of illustration, the drawings show the radiation source 30 and the radiation sensor 40 positioned adjacent the weight-measuring device 20 and the thickness-parameter-measuring device 60, i.e., within the soot deposition area. The radiation source 30 and the radiation sensor 40 could be positioned within the soot deposition area so that attenuation measurements could be made during the formation of the soot preform 12. It is preferred, however, to position the radiation source 30 and the, radiation sensor 40 outside the soot deposition area and to take the attenuation measurements through a longitudinally central portion of the soot preform 12 after it is completely formed.

The determination device 50 receives the signals from the weight-measuring device 20, sensor 64 of the thickness-parameter-measuring device 60, and radiation sensor 40, and determines a concentration of dopant in the soot. The manner in which the dopant concentration is determined will be explained below in more detail with reference to the preferred penetrating radiation, i.e., X rays.

As X rays penetrate matter, they may be absorbed (Einstein photoelectric effect), elastically scattered (Rayleigh), inelastically scattered (Compton) or pass unaffected. Intensity is attenuated exponentially with thickness:

$$dI = -I\mu dt \quad (1)$$

where:
l=initial intensity of the X rays illuminating the preform;
$\mu$=a linear attenuation coefficient for the matter, which gives attenuation per unit thickness ($cm^{-1}$); and
t=path length of the X rays through the matter.

Integration of equation (1) yields Lambert's law:

$$l/l_o = \exp(-\mu t) \qquad (2)$$

where:
l=measured intensity of the X rays passing through the material;
$l_o$=initial intensity of the X rays illuminating the preform; and
t=path length (cm) of the X rays through the matter.

The linear attenuation coefficient $\mu$ is the product of the mass attenuation coefficient $\mu_{mass}$ ($cm^2$/gram) and density $\rho$ (gram/$cm^3$):

$$\mu_{mass} = \mu/\rho \qquad (3)$$

Accordingly, Lambert's law may be rewritten as follows:

$$l/l_o = \exp(-\mu_{mass}\rho t) \qquad (4)$$

For ease of explanation, all subsequent occurrences of $\mu$ shall refer to $\mu_{mass}$.

The mass attenuation coefficient for a compound is the mass weighted sum of attenuation caused by each of the elements (A, B, . . . N) in the compound:

$$\mu_{(A, B, \ldots N)} = (W_A\mu_A) + (W_B\mu_B) + \ldots (W_N\mu_N) \qquad (5)$$

where:
W=weight fraction of the element.

Thus, for example, the mass attenuation coefficient of silica ($SiO_2$), in which the mass fraction of Si and O are 0.4674 and 0.5326, respectively, can be determined as follows:

$$\mu_{SiO2} = 0.4674\mu_{Si} + 0.5326\mu_O \qquad (6)$$

Equation (6) can be readily solved because mass attenuation coefficients for elements have been compiled in tables, such as S. M. Seltzer, Calculation of Photon Mass Energy-Transfer and Mass Energy-Absorption Coefficients, Radiation Research, Vol. 136, 147–170 (1993).

Mass attenuation coefficients can be calculated for mixtures by mass weighting the mass attenuation coefficients of the components (1, 2, . . . N) of the mixture:

$$\mu_{mixture} = (W_1\mu_1) + (W_2\mu_2) + \ldots (W_N\mu_N) \qquad (7)$$

Thus, in a mixture containing $GeO_2$ and $SiO_2$:

$$\mu_{mixture} = (W_{GeO2}\mu_{GeO2}) + (W_{SiO2}\mu_{SiO2}) \qquad (8)$$

Since $W_{GeO2} + W_{SiO2} = 1$, equation (8) can be rewritten as follows:

$$\mu_{mixture} = (W_{GeO2}\mu_{GeO2}) + ((1-W_{GeO2})\mu_{SiO2}) \qquad (9)$$

Substituting equation (9) into equation (4) results in the following equation:

$$l/l_o = \exp(-((W_{GeO2}\mu_{GeO2}) + ((1-W_{GeO2})\mu_{SiO2}))\rho t) \qquad (10)$$

If the material being evaluated contains multiple segments, the total fraction of radiation passing through the soot preform 12 is the product of fractions passing through each segment (1, 2, . . . N):

$$(l/l_o)_{total} = (l/l_o)_1 (l/l_o)_2 \ldots (l/l_o)_N \qquad (11)$$

$$(l/l_o)_{total} = \exp(-\mu_{(1)}\rho_{(1)}t_{(1)}) \exp(-\mu_{(2)}\rho_{(2)}t_{(2)}) \ldots \exp(-\mu_{(N)}\rho_{(N)}t_{(N)}) \qquad (12)$$

$$(l/l_o)_{total} = \exp(-((W_{GeO2}\mu_{GeO2}) + ((1-W_{GeO2})\mu_{SiO2}))_{(1)}\rho_{(1)}t_{(1)}) \exp(-((W_{GeO2}\mu_{GeO2}) + ((1-W_{GeO2})\mu_{SiO2}))_{(2)}\rho_{(2)}t_{(2)}) \ldots \exp(-((W_{GeO2}\mu_{GeO2}) + ((1-W_{GeO2})\mu_{SiO2}))_{(N)}\rho_{(N)}t_{(N)}) \qquad (13)$$

Equations (10) and (13) require attenuation $l/l_o$ density $\rho$, and path length $t$ to determine dopant concentration $W_{GeO2}$. The measurements performed by the apparatus 10 provide all the information needed to determine attenuation $l/l_o$, density $\rho$, and path length t. Thus, the determination device 50 can use equations (10) and (13) to determine the dopant concentration $W_{GeO2}$ in a soot preform 12.

The above treatment assumes monochromatic X rays. For polychromatic X-ray sources, such as X-ray tubes, one may choose to treat the polychromatic output as monochromatic by assuming an "effective wavelength," or one may consider attenuation at particular energy intervals (choosing mass attenuation coefficients appropriately) and computing total attenuation by summation.

As a specific example, the $SiO_2/GeO_2$ soot preform 12 shown in FIGS. 3 and 4 has been completely formed and includes segments 1, 2, . . . N−1, N. As used herein, the term segment refers to any portion of the soot preform 12 for which weight and a thickness parameter can be determined from the weight and thickness parameter measurements made by the apparatus 10. For example, if the weight and thickness parameter of a single soot layer can be determined, that soot layer can constitute a segment. Of course, a plurality of soot layers could also form a segment.

In this preferred embodiment, the weight and thickness parameter of the soot preform 12 were measured by the weight-measuring device 20 and the thickness-parameter-measuring device 60, respectively, at least as frequently as each time a segment (1, 2, . . . N−1, N) was added to the soot preform 12. The weight of an individual segment can be determined as the difference between the weight of the soot preform 12 before and after depositing that segment. Similarly, the thickness parameter T of an individual segment can be determined as the difference between the thickness parameter T of the soot preform 12 before and after depositing that segment.

The apparatus 10 begins by determining the dopant concentration $W_{GeO2(N)}$ in the outermost segment N. Initially, X-ray attenuation $l/l_o$, caused by segment N is determined by irradiating the segment N with X rays from the radiation source 30 and measuring the intensity of the X rays that pass through segment N with the radiation sensor 40, as shown in FIG. 3.

Since only a single soot segment N causes the attenuation, the determination device 50 determines the dopant concentration $W_{GeO2(N)}$ by solving the attenuation equation (10). Solving equation (10) to determine dopant concentration $W_{GeO2(N)}$ requires, in addition to attenuation $l/l_o$, the density $\rho_N$ of segment N and the path length $t_N$ of the X rays through segment N. The determination device 50 uses conventional mathematics to determine density $\rho_N$ based on the weight of segment N, the thickness parameter of segment N, and the length of the soot preform 12 (which can be assumed or measured by conventional means (not shown)). The determination device 50 also uses conventional mathematics to determine the path length $t_N$ based on the spatial relationship between the radiation source 30, the radiation sensor 40, and the soot preform 12, and the thickness parameter $T_N$ of the soot preform 12.

The determination device 50 then determines the dopant concentration $W_{GeO2(N)}$ by iteratively solving the attenuation equation (10). Specifically, starting with an approximation of dopant concentration $W_{GeO2(N)}$, a predicted attenuation is calculated. After comparing the predicted attenuation to the observed attenuation, the estimate of dopant concentration $W_{GeO2(N)}$ is adjusted and used to compute a new predicted attenuation. This process continues until predicted attenuation and observed attenuation agree. When the predicted and observed attenuation agree, the determination device 50 has determined the dopant concentration $W_{GeO2(N)}$ of segment N.

Moving next to segment N−1, attenuation $1/1_o$ is determined by irradiating the segments N and N−1 with X rays from the radiation source 40, and measuring the intensity of the X rays that pass through those segments with the radiation sensor 40, as shown in FIG. 4.

Since multiple soot segments N−1 and N cause the attenuation, the determination device 50 determines the dopant concentration $W_{GeO2(N-1)}$ by solving the attenuation equation (13). Solving equation (13) for dopant concentration $W_{GeO2(N-1)}$ requires, in addition to attenuation $1/1_o$, the densities $\rho_{N-1}$ and $\rho_N$, the path lengths $t_{N-1}$ and $t_N$, and the dopant concentration $W_{GeO2(N)}$. In the same manner as described above for the single segment N, the determination device 50 uses conventional mathematics to determine the densities $\rho_{N-1}$ and $\rho_N$ and the path lengths $t_{N-1}$ and $t_N$ (the path length $t_N$ is the sum of $t_{N(A)}$ and $t_{N(B)}$). The dopant concentration $W_{GeO2(N)}$ is known from the previously executed determination.

The determination device 50 then determines the dopant concentration $W_{GeO2(N-1)}$ by iteratively solving the attenuation equation (13). Starting with an approximation of dopant concentration $W_{GeO2(N-1)}$, a predicted attenuation is calculated. After comparing the predicted attenuation to the observed attenuation, the estimate of dopant concentration $W_{GeO2(N-1)}$ is adjusted and used to compute a new predicted attenuation. This process continues until predicted attenuation and observed attenuation agree. When the predicted and observed attenuation agree, the determination device 50 has determined the dopant concentration $W_{GeO2(N-1)}$ of segment N−1.

Dopant concentrations for the remaining segments can be determined in succession following the same procedure.

The present invention described above provides methods and apparatus that are believed to determine the concentration of a dopant in a soot preform with greater sensitivity than previously known nondestructive techniques. For example, it is believed that the present invention permits a soot density profile to be determined within ±5% relative and permits dopant concentration to be determined within ±5 to 10% relative.

It will be apparent to those skilled in the art that various modifications and variations can be made in the method and apparatus of the present invention without departing from the scope or spirit of the invention. As an example, instead of determining dopant concentrations of the segments after completion of the soot preform, dopant concentration of each segment could be determined immediately after depositing each segment on the soot preform.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining a concentration of dopant in soot that constitutes at least a portion of a soot preform used to form an optical waveguide, the method comprising the steps of:
   measuring the weight of the soot preform;
   measuring a thickness parameter of the soot preform;
   irradiating the soot with penetrating radiation;
   detecting intensity of penetrating radiation passing through the irradiated soot; and
   determining the concentration of dopant based on the measured weight, the measured thickness parameter, and the detected intensity of penetrating radiation.

2. The method of claim 1, wherein the step of measuring the weight of the soot preform includes measuring the weight of the soot preform a plurality of times during formation of the soot preform.

3. The method of claim 1, wherein the penetrating radiation includes X rays.

4. The method of claim 1, wherein the step of irradiating is performed after the soot preform has been completely formed.

5. The method of claim 1, wherein the step of irradiating is performed after each segment of soot is deposited during formation of the soot preform.

6. The method of claim 1, wherein the step of measuring a thickness parameter of the soot preform includes measuring a thickness parameter of the soot preform a plurality of times during formation of the soot preform.

7. The method of claim 1, further comprising the step of determining a path length of the penetrating radiation through the soot preform, wherein the concentration of dopant is determined based on the detected intensity of penetrating radiation, the measured weight, and the determined path length.

8. A method of determining a concentration of dopant in first and second segments of soot that constitute at least a portion of a soot preform used to form an optical waveguide, the method comprising the steps of:
   measuring the weight of the soot preform after the first segment of soot has been deposited on the soot preform;
   measuring a thickness parameter of the soot preform after the first segment of soot has been deposited on the soot preform;
   measuring the weight of the soot preform after the second segment of soot has been deposited on the soot preform;
   measuring a thickness parameter of the soot preform after the second segment of soot has been deposited on the soot preform;
   irradiating the second segment of soot with penetrating radiation;
   detecting intensity of penetrating radiation passing through the second segment of soot;
   determining the concentration of dopant in the second segment of soot based on the detected intensity of penetrating radiation passing through the second segment of soot and the measured weight and thickness parameter of the soot preform after the second segment of has been deposited on the soot preform;
   irradiating the first and second segments of soot with penetrating radiation;

detecting intensity of penetrating radiation passing through the first and second segments of soot; and determining the concentration of dopant in the first segment of soot based on the detected intensity of penetrating radiation passing through the first and second segments of soot and the measured weight and thickness parameter of the soot preform after the first segment of soot has been deposited on the soot preform.

9. The method of claim 8, wherein the penetrating radiation includes X rays.

10. The method of claim 8, wherein the concentration of dopant in the first segment of soot is determined based on the detected intensity of penetrating radiation passing through the first and second segments of soot, the measured weight and thickness parameter of the soot preform after the first segment of has been deposited on the soot preform, and the determined concentration of dopant in the second segment of soot.

11. An apparatus for determining dopant concentration in soot that constitutes at least a portion of a soot preform used to form an optical waveguide, the apparatus comprising:

a weight-measuring device that measures the weight of the soot preform;

a thickness-parameter-measuring device that measures a thickness parameter of the soot preform;

a radiation source that irradiates the soot with penetrating radiation;

a radiation sensor that detects intensity of penetrating radiation passing through the soot; and a determination device that determines a concentration of dopant in the soot based on the measured weight and thickness parameter, and the detected intensity of penetrating radiation.

12. The apparatus of claim 11, wherein the penetrating radiation includes X rays.

* * * * *